United States Patent [19]

Delannoy

[11] 4,269,181
[45] May 26, 1981

[54] TUBULAR DRESSING WHICH IS COMPLETE BY ITSELF

[75] Inventor: Robert Delannoy, Paris, France

[73] Assignee: Molinier S.A., Loire, France

[21] Appl. No.: 29,522

[22] Filed: Apr. 12, 1979

[30] Foreign Application Priority Data

Apr. 21, 1978 [FR] France ............................... 78 12864

[51] Int. Cl.³ ............................................. A61L 15/00
[52] U.S. Cl. ..................................... 128/156; 128/165
[58] Field of Search ................................ 128/155–156, 128/165–166.5, 169–171, 290 W

[56] References Cited

U.S. PATENT DOCUMENTS

| 663,749 | 12/1900 | Gorse | 128/165 |
|---|---|---|---|
| 2,560,712 | 7/1951 | Bell | 128/165 |
| 3,189,919 | 6/1965 | Chase | 128/165 |
| 3,208,451 | 9/1965 | Porter et al. | 128/290 W |
| 3,458,867 | 8/1969 | Moore et al. | 128/165 |
| 3,724,457 | 4/1973 | Klatte | 128/171 |
| 3,881,473 | 5/1975 | Corvi et al. | 128/156 |
| 3,990,440 | 11/1976 | Gaylord, Jr. | 128/165 |

FOREIGN PATENT DOCUMENTS 245897  1/1926  United Kingdom ..................... 128/165

*Primary Examiner*—C. Fred. Rosenbaum
*Attorney, Agent, or Firm*—Eric P. Schellin

[57] ABSTRACT

A complete tubular dressing wherein one section of the tubular dressing constitutes the dressing proper and another section of the tubular dressing is extensible and is designed to hold the dressing in position on the body of the patient.

8 Claims, 6 Drawing Figures

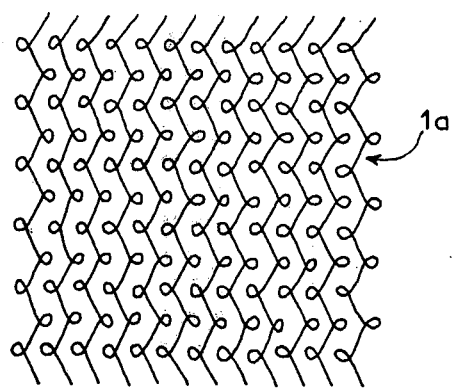
FIG.3
FIG.4
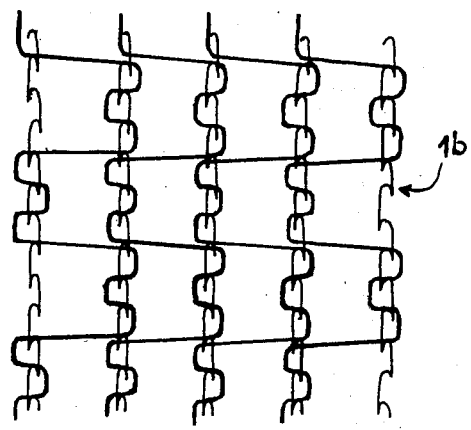

TUBULAR DRESSING WHICH IS COMPLETE BY ITSELF

The present invention relates to a dressing and material for making dressings.

It is known to make tubular bands or covers instead of straight bands to hold compresses, pads, or similar materials onto the area to be treated.

Generally, a complete dressing includes a dressing means, such as a compress, absorbent pad, or the like, as well as a means such as a band, tube, or the like, to hold the dressing means against the body of the patient. This creates problems of availability, increases the costs of the complete dressing, and makes dressing the patient time-consuming and difficult.

The complete tubular dressing of the present invention eliminates these problems. The complete tubular dressing of the present invention is characterized in that a section of the tubular dressing of the present dressing is woven, knitted, etc. to constitute the dressing proper (compress, absorbent pad, or the like), and the other section of the tubular dressing of the present invention is woven, knitted, or the like, so as to have an elastic or extensible capacity which is sufficient to hold the dressing rigidly in position on the body of the patient.

These and other characteristics will be more fully understood in the course of the following description, with reference to the attached drawings wherein there is shown an embodiment of the dressing according to the invention. The drawing is by way of example, not by way of limitation.

IN THE DRAWINGS:

FIG. 3 is a view of a knitted weave dressing part of the tubular dressing.

FIG. 4 is a view of an open chain weave of the positioning part of the tubular dressing.

Figure 1:
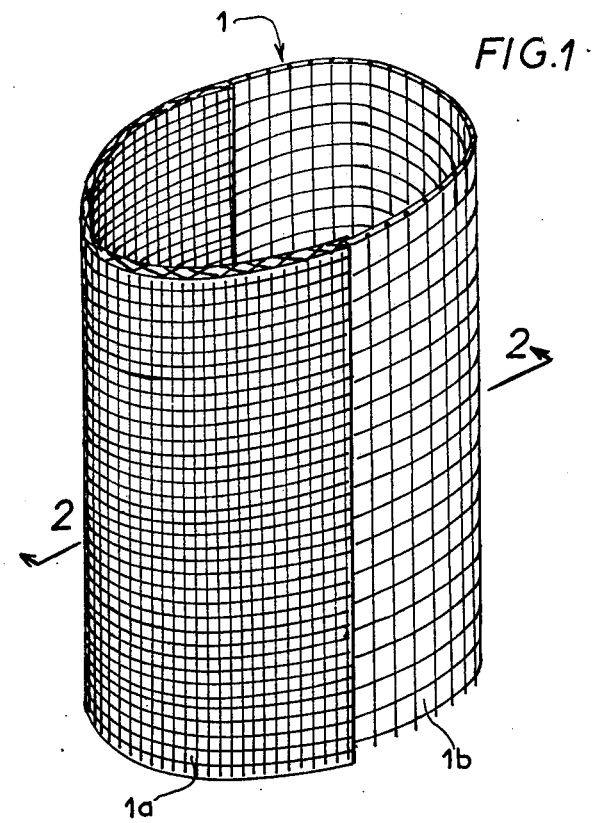
FIG. 1 is a perspective view of one embodiment of the complete tubular dressing in accordance with the invention.
Figure 5:
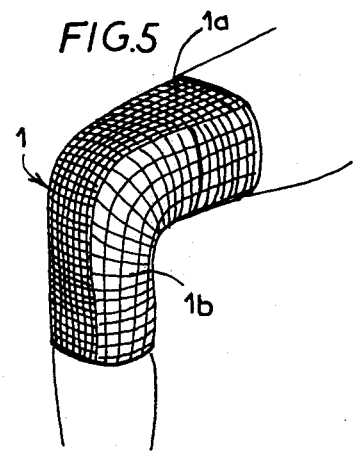
FIG. 5 is a perspective view of a complete tubular dressing positioned around a knee of a patient.

The object of the invention will be made more apparent in describing it in the embodiment shown by way of example in the figures of the drawing.

The complete tubular dressing 1 includes a dressing part 1a and a positioning part 1b.

It will be apparent that the dressing part 1a and the positioning part 1b can form greater or lesser parts of the entire tube, and that various types of dressings may be used in accordance with the lengths necessary for any use.

The part 1a which is intended to constitute the dressing proper is generally not extensible or very slightly extensible. This part is preferably made of hydrophilic filaments, such as hydrophilic cotton, hydrophilic fibrane, or other hydrophilic materials, including nonwoven hydrophilic material. It is also possible, for some applications, to make part 1a of a hydrophobic (non-absorbent) material, in order to facilitate the healing of various wounds. An example of a hydrophobic material is polypropylene, known under the trade-name "MERKALON."

Part 1a can be made by weaving, knitting, or by other methods. Alternatively, part 1a can also be made of nonwoven materials (bonded fibrous materials).

In any case, part 1a must have a compact structure, whether knitted, woven, or nonwoven, to ensure a substantial absorbent capacity, as this is generally required.

There may be seen in FIG. 3 an embodiment of part 1a with a knitted weave providing a convenient capacity to the structure. No further details are necessary concerning such a knitted weave, which is well known to those skilled in the art. This is merely an example of one embodiment of the invention.

Figure 6:
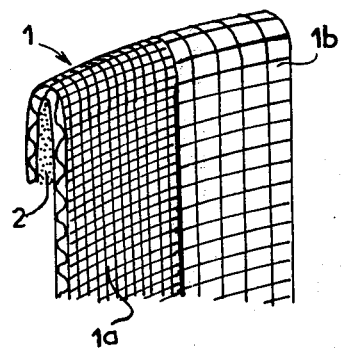
FIG. 6 shows the tubular dressing folded over on itself to increase the absorbent effect of the dressing part, wherein one or more medicinal products may be placed between the absorbing layers.
Figure 2:
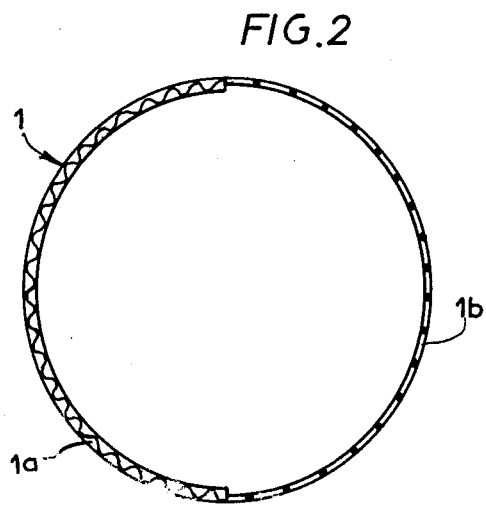
FIG. 2 is an enlarged view along line 2—2 of FIG. 1.

To increase the absorbent capacity of part 1a, it is possible to fold the tubular dressing over on itself one time, as shown in FIG. 6, or even more than one time.

Folding over of the dressing on itself makes it possible, as desired, to place between the absorbent layers of part 1a some medicinal products for treatment (of scalds, for instance) or additional absorbent materials (hydrophilic cotton, nonwoven material, or the like). It is thus possible to make dressings ready for use, more particularly in case of emergency.

In contrast to the non-extensible dressing part, positioning part 1b must be quite extensible or quite elastic. Because of this function, part 1b is knitted or woven with a texture which is quite loose and quite exposed.

FIG. 4 shows an embodiment wherein part 1b is made of an open chain and binding weave corresponding to the above characteristics of this part. This weave is shown by example only, and is well known by those skilled in the art. Therefore, further details of this embodiment are not necessary. The entire tubular dressing can be woven or knitted in one piece, in a conventional manner.

It is within the scope of the invention to make the complete tubular dressing by separately manufacturing parts 1a and 1b and assembling them afterwards by gluing or stitching. This is particularly useful when part 1a is made of nonwoven material.

The advantages of the complete tubular dressing made according to the present invention include:
 easier dressing of wounds
 convenience and speed in positioning the dressing
 cost savings over conventional dressing arrangements.

It will be understood that the invention is in no way limited to the particular embodiments described above, and that alternative arrangements for the dressing do not constitute a departure from the scope of the invention.

I claim:

1. A complete tubular dressing in one piece comprising one sector forming a dressing proper and one section made of extensible material which is sufficient to hold the dressing securely on the body of a patient, wherein the dressing proper is made of woven hydrophilic material.

2. The complete tubular dressing of claim 1 wherein the fibers of the dressing proper are selected from the group consisting of cotton and fibrane.

3. The complete tubular dressing of claim 1 wherein the dressing proper is folded over on itself at least one time, forming at least one space between the folds.

4. The complete tubular dressing of claim 3 wherein the space between the folds contains medicinal material.

5. The complete tubular dressing of claim 4 wherein the space between the folds also contains absorbent material.

6. The complete tubular dressing of claim 3 wherein the space between the folds contains absorbent material.

7. The complete tubular dressing of claim 1 wherein the section made of extensible material is made of open chain weave.

8. The complete tubular dressing of claim 1 wherein the dressing is woven in one piece.

* * * * *